(12) United States Patent
Lomick

(10) Patent No.: US 9,345,829 B2
(45) Date of Patent: May 24, 2016

(54) INFUSION DEVICE FOR IV DRUGS THAT ARE INCOMPATIBLE TO EACH OTHER

(71) Applicant: Joe Lomick, Durham, NC (US)

(72) Inventor: Joe Lomick, Durham, NC (US)

( * ) Notice: Subject to any disclaimer, the term of this patent is extended or adjusted under 35 U.S.C. 154(b) by 178 days.

(21) Appl. No.: 14/262,786

(22) Filed: Apr. 27, 2014

(65) Prior Publication Data

US 2015/0306309 A1 Oct. 29, 2015

(51) Int. Cl.
*A61M 5/00* (2006.01)
*A61M 5/168* (2006.01)
*A61M 5/14* (2006.01)
*A61M 39/24* (2006.01)

(52) U.S. Cl.
CPC .......... *A61M 5/16827* (2013.01); *A61M 5/1408* (2013.01); *A61M 39/24* (2013.01); *A61M 2039/242* (2013.01)

(58) Field of Classification Search
CPC .......... A61M 2039/242; A61M 39/24; A61M 5/1408; A61M 5/16827
USPC .................................................. 604/246–249
See application file for complete search history.

(56) References Cited

U.S. PATENT DOCUMENTS

| | | | | |
|---|---|---|---|---|
| 3,227,173 A * | 1/1966 | Bernstein | ................ | A61M 5/40 128/114.1 |
| 5,279,557 A * | 1/1994 | Lomick | ............... | A61M 5/1408 604/254 |
| 6,099,512 A * | 8/2000 | Urrutia | ............... | A61M 5/1411 604/251 |
| 2003/0017068 A1* | 1/2003 | Larrain | ............. | A61M 5/16827 417/567 |
| 2005/0273062 A1* | 12/2005 | Franksson | ........... | A61M 5/1411 604/254 |
| 2005/0283123 A1* | 12/2005 | Lyde | ....................... | A61M 5/40 604/254 |

\* cited by examiner

*Primary Examiner* — Rebecca E Eisenberg
(74) *Attorney, Agent, or Firm* — John L Sotomayor

(57) ABSTRACT

The present invention is a device and system to permit the isolation of two fluid compounds to be delivered to a patient without intermingling the two fluid compounds, yet permitting the labor saving activity of permitting a nurse or other medical staff member to hang two IV bags simultaneously. Fluid from the first IV bag inflates the barrier pressure valve and seals the system against the intrusion of the second fluid from the second IV bag until the first fluid has been fully delivered. The barrier pressure valve then unseals the system to permit the flow of fluid from the second IV bag to the patient. This implementation permits this isolation and separate delivery of two fluids without using electronics or other technology that would require a battery backup or other uninterruptible power source.

18 Claims, 6 Drawing Sheets

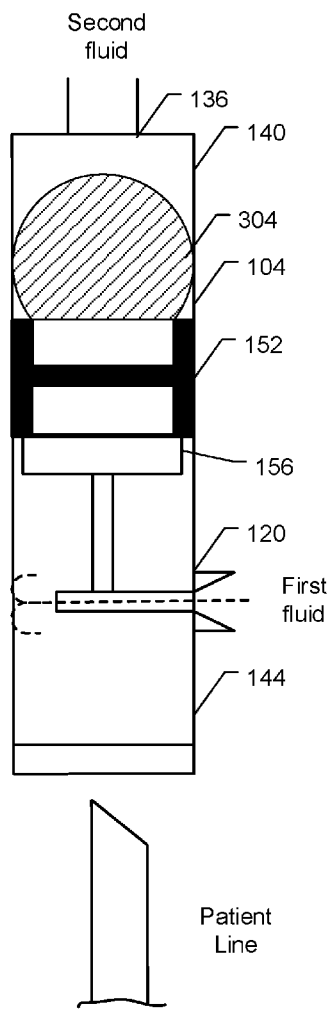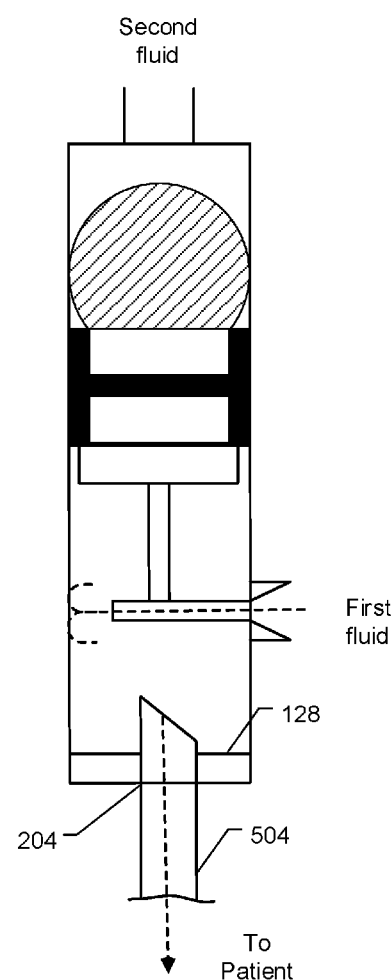
Figure 4
Figure 5

INFUSION DEVICE FOR IV DRUGS THAT ARE INCOMPATIBLE TO EACH OTHER

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

In any administration of multiple intravenous (IV) medications, drugs, or other compounds there is a concern that incompatibilities between the medications being introduced to the patient will cause harm. This is especially true of patients in intensive care units, as these patients typically receive multiple IV medications, drugs, or other compounds from two or more IV drip bags simultaneously. Reducing the instance of problems due to unwanted incompatibilities can be assisted by isolating the introduction of multiple medications, drugs or other compounds. This can be done while still permitting a nurse or other medical staff member to reduce the amount of labor required by hanging two IV drip bags at the same time in a manner that permits the isolation of each fluid medication, drug, or compound from any other.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which:

FIG. 4 is a view of the barrier pressure valve isolating the delivery of a first fluid compound consistent with certain embodiments of the present invention.

FIG. 5 is a view of the barrier pressure valve in operation delivering a first fluid compound to a patient consistent with certain embodiments of the present invention.

DETAILED DESCRIPTION

Figure 1:
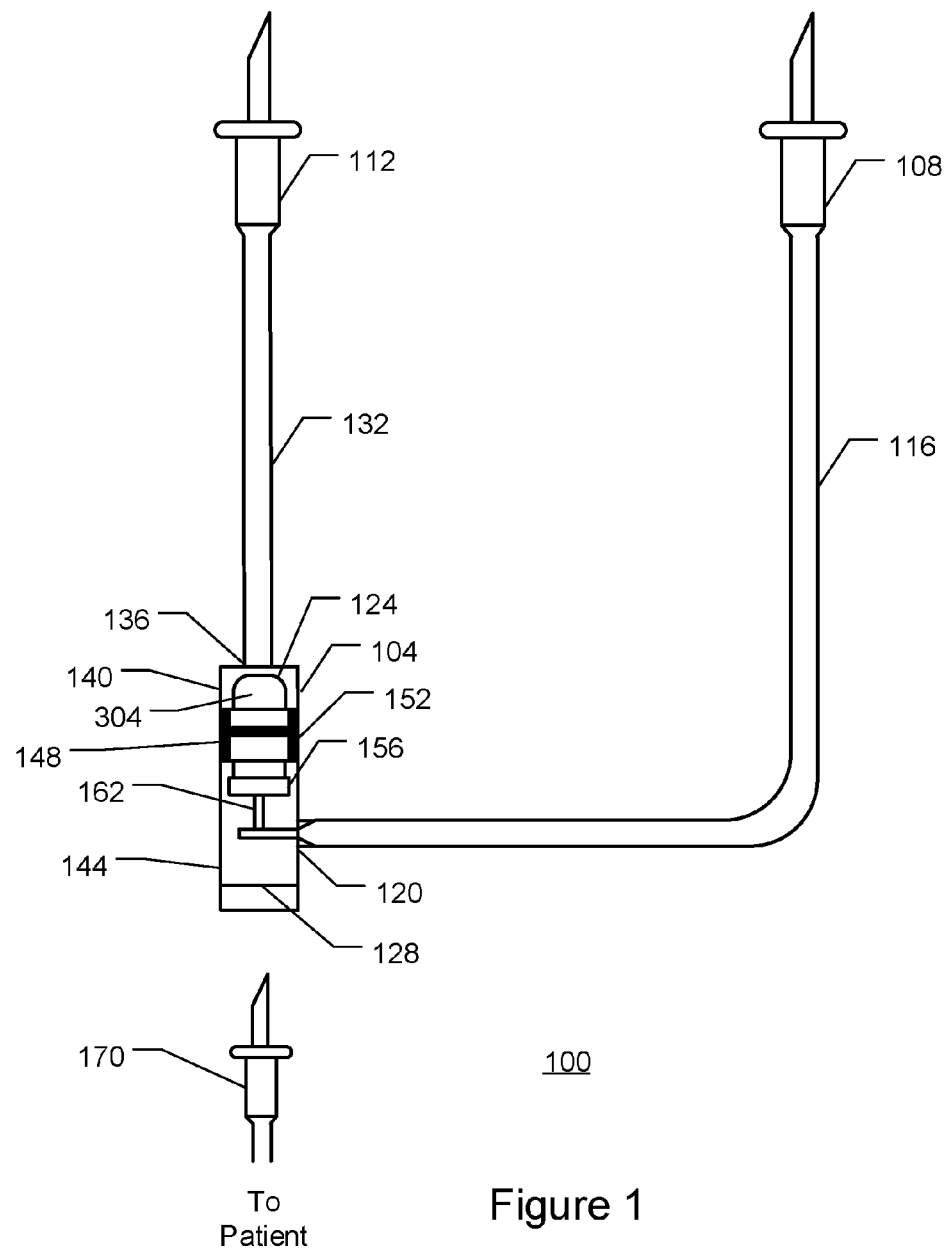
FIG. 1 is a view of a barrier pressure valve and spikes for two IV bags containing separate fluid compounds consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one, or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an exemplary embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to an IV is indicative of an Intra-Venous delivery system for the perfusion of drugs, medications or other compounds suspended in fluid that must be delivered directly into the veins of a patient. An IV spike references a sharpened, hollow tube of any material that is sufficient to pierce the container of a fluid drug, medication, or other compound and provide egress from the container into the tube of which the IV spike forms at least one end. An IV bag references a container, composed of any material such as plastic, mylar, rubber, or any other material, natural or synthetic, that may be pierced by an IV spike, that contains a fluid drug, medication, or other compound. Additionally, an IV bag may have a handle or other means for placing on a hook or other structure so as to suspend the IV bag in a position to permit the flow of the fluid drug, medication or other compound from the IV bag position to another physical position using the force of gravity. A Y-site adaptor references a connection point for two tubes forming the top part of the Y to join together at the adaptor site to lead into and become a single tube. A Y-site adaptor is typically used as a delivery mechanism to permit two separate fluids, such as drugs, medications or other compounds, in two separate IV bags to be delivered to a patient simultaneously.

The perfusion of two fluid compounds, such as drugs, medications, or other compounds in fluid form, into a patient is typically accomplished through the use of a Y-site adaptor. The two separate fluids flow at the same time from the two tubes at the top of the Y-site adaptor into the single tube that forms the bottom part of the Y-site adaptor. Because the two fluids flow together it is difficult to determine how much of each of the two fluids from either IV bag is being administered at a given time. An additional problem is that if there are incompatibilities between the two fluids, whether they are drugs, medications, or other compounds suspended in fluid, the fluids are still delivered simultaneously and a patient may suffer a reaction to the erroneous simultaneous delivery of incompatible compounds.

One object of the present invention is to permit the isolation of two fluid compounds to be delivered to a patient without intermingling the two fluid compounds, yet permitting the labor saving activity of permitting a nurse or other medical staff member to hang two IV bags simultaneously. An additional object of the present invention is to permit the isolation of delivered fluids such that dosage may be determined and measured with accuracy as each fluid is delivered without mixing with any other fluid. Another object of the present invention is to permit this isolation and separate delivery of two fluids without using electronics or other technology that would require a battery backup or other uninterruptible power source. This implementation reduces the complexity of the device, permitting the device to continue operating when there is no electric power available, and keeping the cost of the device at a reasonable level.

A device for isolated delivery of fluid compounds is disclosed herein, having a main chamber having a top portion, barrier portion, and bottom portion, where the main chamber has at least two entry points and one exit point for fluid flow. A barrier pressure valve installed wholly within the main chamber is positioned to permit the barrier pressure valve to move vertically through an opening in the center of the barrier portion of the main chamber. The barrier pressure valve has a flexible portion and a rigid portion and is positioned such that when the flexible portion is filled with a fluid, the flexible portion is above the barrier portion of the main chamber and contained within the top portion of the main chamber. The flexible portion of the barrier pressure valve is sufficiently flexible to inflate under the pressure of a fluid introduced to the main chamber and causes the barrier pressure valve to isolate the top portion of the main chamber from the bottom portion of the main chamber such that no fluid may flow from the top portion of the main chamber to the bottom portion of the main chamber.

In an embodiment, the top portion, barrier portion, and bottom portion of the main chamber are arranged vertically, with the top portion at the top, the bottom portion at the bottom and the top portion separated from the bottom portion by the barrier portion when the main chamber is held upright, and the entire device is composed of materials that may be sterilized such that the device is entirely sterile prior to use. In addition, the barrier portion of the main chamber has an exterior cross section having the same cross section or diameter as the exterior cross section or diameter as the top and bottom portions of the main chamber, and the barrier portion has an internal cross section or diameter that is smaller than the interior cross section or diameter of the top and bottom portions of the main chamber. The barrier portion of the main chamber has an opening in the center of the barrier portion and a barrier pressure valve is positioned entirely within the main chamber and positioned to move vertically through an opening in the center of the barrier portion of the main chamber.

The main chamber has a first entry point for fluid flow positioned in the side wall of the bottom portion of the main chamber, a second entry point for fluid flow positioned at the top edge of the top portion of the main chamber, and an exit point for fluid flow positioned at the bottom edge of the bottom portion of the main chamber. The bottom portion of the main chamber has a flexible plastic membrane positioned vertically between the first entry point and the bottom edge of the bottom portion of the main chamber. The barrier pressure valve has a flexible portion and a rigid portion, where the flexible portion is sufficiently flexible to inflate under the pressure of incoming fluid and come into contact with the interior surface of the top portion of the main chamber to form a seal between the flexible portion of the barrier pressure valve and the top portion of the main chamber that prevents the flow of fluid past the barrier pressure valve flexible portion.

In an embodiment, there is a system for isolated delivery of fluid compounds, having a main chamber with a top portion, barrier portion, and bottom portion. The main chamber has at least two entry points and one exit point for fluid flow, with a barrier pressure valve installed wholly within the main chamber and positioned to permit the barrier pressure valve to move vertically through an opening in the center of the barrier portion of the main chamber. The barrier pressure valve has a flexible portion and a rigid portion and the barrier pressure valve positioned such that when the flexible portion is filled with a fluid, the flexible portion is above the barrier portion of the main chamber and is contained within the top portion of the main chamber and the rigid portion is in contact with the barrier portion of the main chamber. The flexible portion of the barrier pressure valve is sufficiently flexible to inflate under the pressure of a fluid introduced to the main chamber and cause the barrier pressure valve to isolate the top portion of the main chamber from the bottom portion of the main chamber such that no fluid may flow from the top portion of the main chamber to the bottom portion of the main chamber.

In an exemplary embodiment, the invention is a device that permits the simultaneous hanging of two IV bags while isolating the delivery of the fluid within each IV bag such that the fluids in the two bags are delivered in a serial fashion, first one fluid and then the second fluid, without intermingling the fluids prior to delivery to the patient. In this exemplary embodiment, the device does not require the use of electricity or control circuitry of any kind. In operation, a medical staff person attaches an IV bag containing one fluid to the device by pushing a first input IV spike through the sidewall of the IV bag and attaches a second IV bag containing a second fluid to the second input IV spike, then attaching an IV line to the exit port of the invention. The invention will regulate the fluids flowing from the two IV bags automatically, without further intervention by a medical staff member.

In this exemplary embodiment, the flow of the fluids from the two connected IV bags is regulated by the invention through the use of a barrier pressure valve. The barrier pressure valve is installed within the main chamber of the device, and the main chamber of the device is sealed from the outlet port through the use of a plastic membrane. The main chamber has two inlet ports, one at the top of the main chamber and a second inlet port that attaches at one side of the main chamber. The top inlet port is above the structure of the barrier pressure valve, and the side inlet port is positioned below the structure of the barrier pressure valve. The positioning of the inlet ports and structure of the barrier pressure valve will be discussed in greater detail in combination with the figures below.

In operation, a first fluid enters the main chamber through the side inlet port. Because the outlet port is sealed, the first fluid fills the main chamber and causes the inflation of the barrier pressure valve. The barrier pressure valve is pushed up moving vertically upward through an opening in the barrier stop structure as the first fluid fills the main chamber until the bottom edge of the barrier pressure valve presses against the bottom of the barrier stop structure. The barrier pressure valve is held in place by the barrier stop structure, but continues to inflate under the pressure of the incoming first fluid until the portion of the barrier pressure valve positioned above the barrier stop structure presses against the sides of the top of the main chamber above the barrier stop structure. The inflation of the barrier pressure valve isolates the lower portion of the main chamber and limits the fluid flow into the main chamber to the first fluid entering through the side inlet. The medical practitioner may then attach a second IV bag to the IV spike connected to the tube that attaches to the top inlet port at the top of the chamber, and above the barrier pressure valve. The fluid from the second IV bag will begin to flow into the top portion of the main chamber, but will be stopped from entering the bottom portion of the main chamber by the inflated barrier pressure valve. This action isolates the fluid from the first IV bag entering through the side inlet to the main chamber from the fluid flowing from the second IV bag, entering through the top inlet to the main chamber.

The medical practitioner may now use an IV spike to pierce the plastic barrier at the bottom of the main chamber. The IV spike piercing the plastic barrier permits the flow of the first fluid through the outlet port positioned at the bottom of the main chamber directly to a patient. The barrier pressure valve remains inflated, restricting the flow of fluid to that fluid from the first IV bag entering through the side inlet, until the first IV bag is substantially empty and the barrier pressure valve deflates. The barrier pressure valve begins to move downward vertically as the pressure of the second fluid becomes sufficient to push the barrier pressure valve down and away from the barrier stop structure. With the barrier pressure valve now moved away from the barrier stop structure, the second fluid, entering through the top inlet port of the main chamber, has a flow pathway from the top inlet port, through the main chamber and down through the outlet port to the IV line connected to the patient.

This action begins the flow of the second fluid from the second IV bag to the patient without further interaction from the medical staff member. Additionally, because the flow of the second fluid cannot begin until the main chamber and barrier pressure valve are substantially empty of the first fluid, the fluids do not intermingle and each compound remains isolated from the other. In this manner the invention delivers two fluids in a serial fashion, permitting the accurate dispensation of a known amount of the fluid compound and keeping the two fluids substantially isolated. This action permits a medical staff member to attach two IV bags containing two fluids that may have known mixing incompatibility to a single delivery device and system without fear of the two fluids mixing or intermingling as would be the case with an IV delivery device having a simple Y-site delivery portion.

The structure of the device is simple, having only one moving part; the barrier pressure valve. Because of the simplicity of the structure, having only one moving part, the device may be manufactured inexpensively. Therefore, the device herein described may be manufactured as a sterile, disposable, inexpensive, one use product.

Turning now to FIG. 1, in an exemplary embodiment the invention is presented in its entirety 100. The invention has a main chamber 104 in which the structural elements are enclosed. The main chamber 104 in an exemplary embodiment has a circular cross-section, however, this should in no way be considered limiting as in other embodiments the main chamber may be square, rectangular, or have any cross section shape that is consistent with sealing the chamber against fluid loss when in use. Fluid compounds, such as drugs, medications or other compounds in liquid form are introduced in a serial fashion through a first IV spike 108 and a second IV spike 112. In this exemplary embodiment, first and second IV bags may be suspended from an IV hanger or other structural element (not shown) intended to keep the IV bags at a physical location vertically above the physical location of a patient. The first IV spike 108 is connected to the main chamber 104 through a flexible tube 116 made of plastic or other material that may be sterilized prior to use. The connection point 120 for the flexible tube 116 that connects the first IV spike 108 to the main chamber 104 is at the side of the main chamber 104 and must be positioned below the bottom edge of the barrier pressure valve 124 and above a flexible plastic membrane 128 when the main chamber 104 is positioned vertically. A second flexible tube 132 is connected to the main chamber 104 at a top opening 136 which is the connection point at the center of the top side of the main chamber 104 when the main chamber 104 is positioned vertically.

The main chamber 104 is composed of a top portion 140, a bottom portion 144, and a barrier portion 148. The top portion 140 of the main chamber 104 is connected to the barrier portion 148 and to the bottom portion 144 through the use of a strong adhesive that bonds the three portions of the main chamber 104 together. The adhesive used forms a bond that will not dissolve when exposed to liquids that are suitable for infusion into a human body, and forms a tight seal that does not leak or otherwise impair the integrity of the main chamber. Such adhesives are known in the art and will not be further described herein. The interior cross section of the barrier portion 148 is smaller than the interior cross section of the main chamber 104. The barrier portion 148 has a center opening of sufficient size and cross section to permit the main portion of the barrier pressure valve 124 to pass through the barrier portion 148 center opening. The barrier pressure valve 124 has a base portion 156 that is larger in cross section size than the center opening such that when the barrier pressure valve moves upward vertically in response to the introduction of a first fluid into the bottom part 144 of the main chamber 104, the barrier pressure valve base portion 156 will come into contact with the barrier portion 148 and be unable to move any further than the bottom of the barrier portion 148. When the bottom portion 144 of the main chamber is empty of any fluid the barrier pressure valve 124 rests on the barrier pressure valve support 162. The bottom portion 144 of the main chamber 104 provides access to the fluid or fluids that flow through the main chamber 104 by the introduction of an IV spike 170 through an access point in the bottom portion 144 which then pierces the plastic membrane 128 to permit fluid to flow from the main chamber through a tube connected to the IV spike 170 and then to a patient.

Figure 2:
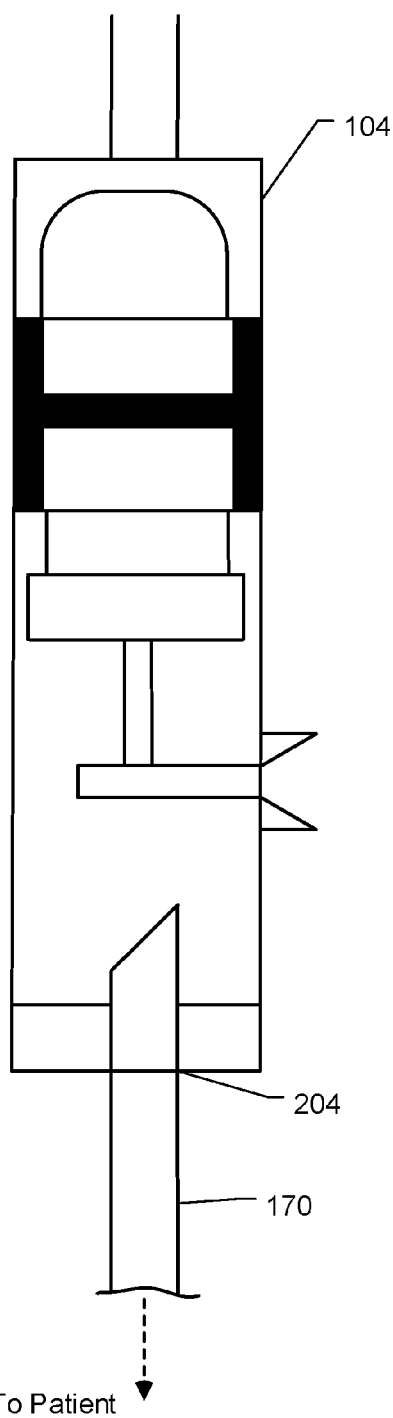
FIG. 2 is a view of the barrier pressure valve connection to a patient consistent with certain embodiments of the present invention

Turning to FIG. 2, is an expanded view of an exemplary implementation of the main chamber 104 of the invention with an IV spike 170 connected to an IV line leading to a patient inserted into the bottom access point 204 of the main chamber 104. In this embodiment, the fluid will flow from the main chamber 104 down through the IV spike 170 through the influence of gravity. There are no electronic or electrical pumps or controls needed to permit the action of fluid flow from the main chamber 104 to the patient. In this manner, the invention permits the continuous infusion of fluids from the main chamber 104 of the invention to a patient regardless of the state of power or lack of power to the facility in which the invention is being used.

Figure 3:
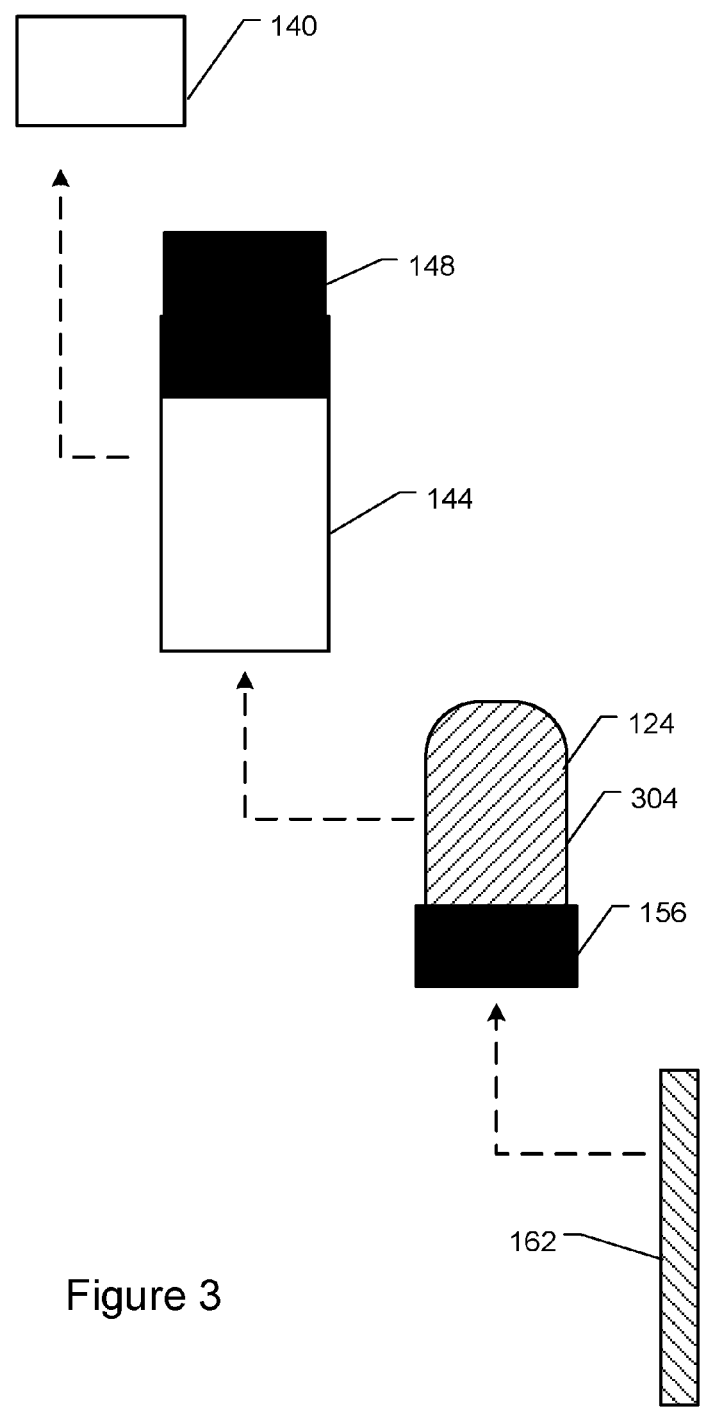
FIG. 3 is a view of the internal component of a barrier pressure valve structure consistent with certain embodiments of the present invention.

Turning now to FIG. 3, this figure presents the internal components of the barrier pressure valve 124 and main chamber 104 structure consistent with certain embodiments of the present invention. The top portion 140 of the main chamber 104 forms the upper structure of the main chamber 104 when the invention is positioned vertically, and is the part of the structure into which the barrier portion 148 is fitted when the main chamber 104 is assembled. The barrier portion 148 is of sufficient cross section to fit within the cross section area of the top portion 140 and the bottom portion 144 of the main chamber 104. The barrier portion 148 outer wall is in contact with the inner wall of the top portion 140 and in contact with the inner wall of the bottom portion 144 along the entire outer wall surface of the barrier portion 148 when inserted into the top portion 140 and bottom portion 144 of the main chamber 104. The barrier portion 148 is permanently attached to the top portion 140 and bottom portion 144 of the main chamber 104 through the use of an adhesive that forms a permanent, fluid proof bond between the barrier portion 148 and the top portion 140 and bottom portion 144 of the main chamber.

The barrier pressure valve 124 is composed of a flexible, inflatable portion 304 and a bottom portion 156. The inflatable portion 304 is composed of an expandable material such as plastic, mylar, rubber or any other material that will expand under the pressure of fluid flowing into the inflatable portion 304. The cross section area of the inflatable portion 304 is of the proper size to permit the inflatable portion to be inserted through a central opening in the barrier portion 148 of the main chamber and permit the free travel of the inflatable portion 304 in a vertical direction through the barrier portion 148 when the inflatable portion 304 is not inflated by a fluid. The bottom portion 156 of the barrier pressure valve 124 size is larger than the cross section area of the central opening of the barrier portion 148, but smaller in cross section that the interior cross section of the bottom portion 144 of the main chamber 104. In a non-limiting example, if the main chamber 104 has a circular cross section, the barrier portion 148 would be of sufficient diameter to fit inside the bottom portion 144 of the main chamber 140, and the barrier portion 148 would have a circular central opening through which the barrier pressure valve inflatable portion 304 would travel freely, and the bottom portion 156 of the barrier pressure valve 124 would be of a slightly larger diameter than the central opening of the barrier portion 148. In this example, the barrier pressure valve 124 would travel upward vertically under the pressure of a fluid entering the bottom portion 144 of the main chamber 104 until the bottom portion 156 came into contact with the bottom of the barrier portion 148, where the vertical motion would stop and the barrier pressure valve 124 would be held in place by the pressure of the fluid in the main chamber 104.

The barrier pressure valve 124 is held in place by a barrier pressure valve support tube 162 when the bottom portion 144 of the main chamber 104 is empty of fluid, or when there is insufficient fluid pressure to force the barrier pressure valve 124 to move vertically. When fully assembled, a plastic membrane 128 (not shown) is installed between the bottom of the barrier pressure valve support tube 162 and the bottom interior surface of the bottom portion 144 of the main chamber 104. The plastic membrane 128 permits incoming fluid to create the pressure necessary to move the barrier pressure valve 124 vertically upwards to a stop against the bottom of the barrier portion 148 of the main chamber 104. Further exemplary configurations of the are discussed below in connection with the figures presented.

Turning now to FIG. 4, this figure presents a view of the barrier pressure valve isolating the delivery of a first fluid compound consistent with certain embodiments of the present invention. In this non-limiting example a first fluid contained within a first IV bag is connected to the main chamber 104 of the invention through the side opening 120. The first fluid flows from the first IV bag into the main chamber 104 through the side opening 120. The first fluid flows into the main chamber 104 and strikes the interior surface of the side of the main chamber 104 at an impact point 404 physically opposite from the side opening 120. The tube from the first IV bag tapers to a diameter that is less than half of the diameter of the tube. This taper causes an increase in pressure of the first fluid as it enters the main chamber 104. The taper of the connecting tube where it enters the main chamber 104 is sufficient to raise the pressure of the incoming first fluid to cause the first fluid to spread from the impact point 404 to fill the main chamber 104 and expand vertically into the barrier pressure valve 124. This pressure causes the flexible, inflatable portion 304 of the barrier pressure valve 124 to expand.

During the inflow of the first fluid, the first fluid fills the inflatable portion 304 of the barrier pressure valve 124 and the barrier pressure valve 124 moves upward vertically through the central opening of the barrier portion 152 of the main chamber 104. The barrier pressure valve 124 moves vertically under the pressure increase of the first fluid as it continues to flow into the main chamber 104 until the bottom portion 156 of the barrier pressure valve 124 contacts the bottom surface of the barrier portion 152. The first fluid continues to flow into the barrier pressure valve 124 causing the flexible portion 304 of the barrier pressure valve 124 to expand until the sides of the flexible portion 304 of the barrier pressure valve 124 contact the interior surface of the top portion 140 of the main chamber 104 and forms a seal to isolate the top portion 140 of the main chamber 104 from the bottom portion 148 of the main chamber 104. The pressure from the inflow of the first fluid is sufficient to overcome the force of gravity pulling on the second fluid as it enters the top portion 140 of the main chamber 104, blocking the flow of the second fluid into the main chamber and keeping the first fluid isolated from the second fluid as the first fluid flows through the main chamber 104.

In this embodiment, the medical practitioner may then connect a second fluid in a second IV bag to the tube that connects into the top portion 140 of the main chamber 104 through the top opening 136. With the flexible portion of the barrier pressure valve 124 fully inflated with the first fluid, the second fluid cannot flow past the barrier pressure valve 124. In this manner, the first fluid flowing into the bottom portion 148 of the main chamber 104 is continuously isolated from the second fluid that is held within the upper portion 148 of the main chamber 104. The barrier pressure valve 124 begins to deflate at the point when just about all of the first fluid from the first IV bag has drained from the main chamber and into the IV line going to the patient from the main chamber 104. By the time the gravitational force pulling on the second fluid from the second IV bag overcomes the barrier pressure valve 124, forcing the barrier pressure valve to move downward vertically, the remaining first fluid from the first IV bag has drained out of the main chamber 104 and into the IV line connected to the patient.

Turning to FIG. 5, this figure presents an exemplary view of the flow of a first fluid from the main chamber 104 of the invention. In this non-limiting example, a patient line is connected to the bottom portion 144 of the main chamber 104 by inserting an IV spike 504 in to the bottom portion 144 of the main chamber 104 through the bottom opening 204. The IV spike 504 enters through the bottom opening 204 and pierces the plastic membrane 128. The first fluid then flows from the bottom portion 144 of the main chamber 104 through the IV spike 504 and into the tube that is connected to the patient. It is important to note that while the first fluid is flowing through the main chamber 104 and through the IV spike 504 to the patient, the barrier pressure valve 124 continues to contain the second fluid in the upper portion 140 of the main chamber 104 to isolate the delivery of first fluid from the second fluid.

Figure 6:
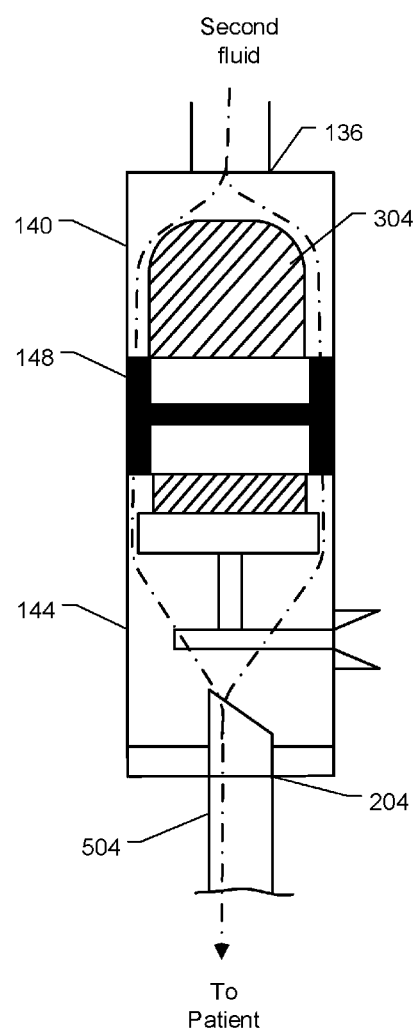
FIG. 6 is a view of the barrier pressure valve in operation delivering a second fluid compound to a patient consistent with certain embodiments of the present invention.

Turning to FIG. 6, this figure presents an exemplary view of the barrier pressure valve in operation delivering a second fluid compound to a patient consistent with certain embodiments of the present invention. The fluid compound in the first IV bag flows to the patient until the first IV bag is substantially empty. As the first fluid compound delivery completes, the first fluid compound drains out of the flexible portion 304 of the barrier pressure valve 124 and the flexible portion 304 deflates. The barrier pressure valve 124 begins to move downward vertically as the pressure of the second fluid becomes sufficient to push the barrier pressure valve 124 down and away from the barrier portion 148 of the main chamber 104. With the barrier pressure valve 124 now moved away from the barrier portion 148, the second fluid, entering through the top opening 136 which serves as the upper inlet port of the main chamber 104, has a flow pathway from the top opening 136, through the main chamber 104 passing around the barrier pressure valve 124 and down through bottom portion 144 of the main chamber 104 to the outlet port 204 and into the IV line 504 connected to the patient. This action begins the flow of the second fluid compound from the second IV bag to the patient without further interaction from the medical practitioner. Additionally, because the flow of the second fluid compound cannot begin until the main chamber 104 and barrier pressure valve 124 are empty of the first fluid compound, the fluid compounds do not intermingle and each compound remains isolated from the other. In this manner the invention delivers two fluids in a serial fashion, keeping the two fluids isolated and permitting a medical practitioner to attach two IV bags containing two fluid compounds that may have known mixing incompatibility to a single delivery device.

Figure 7:
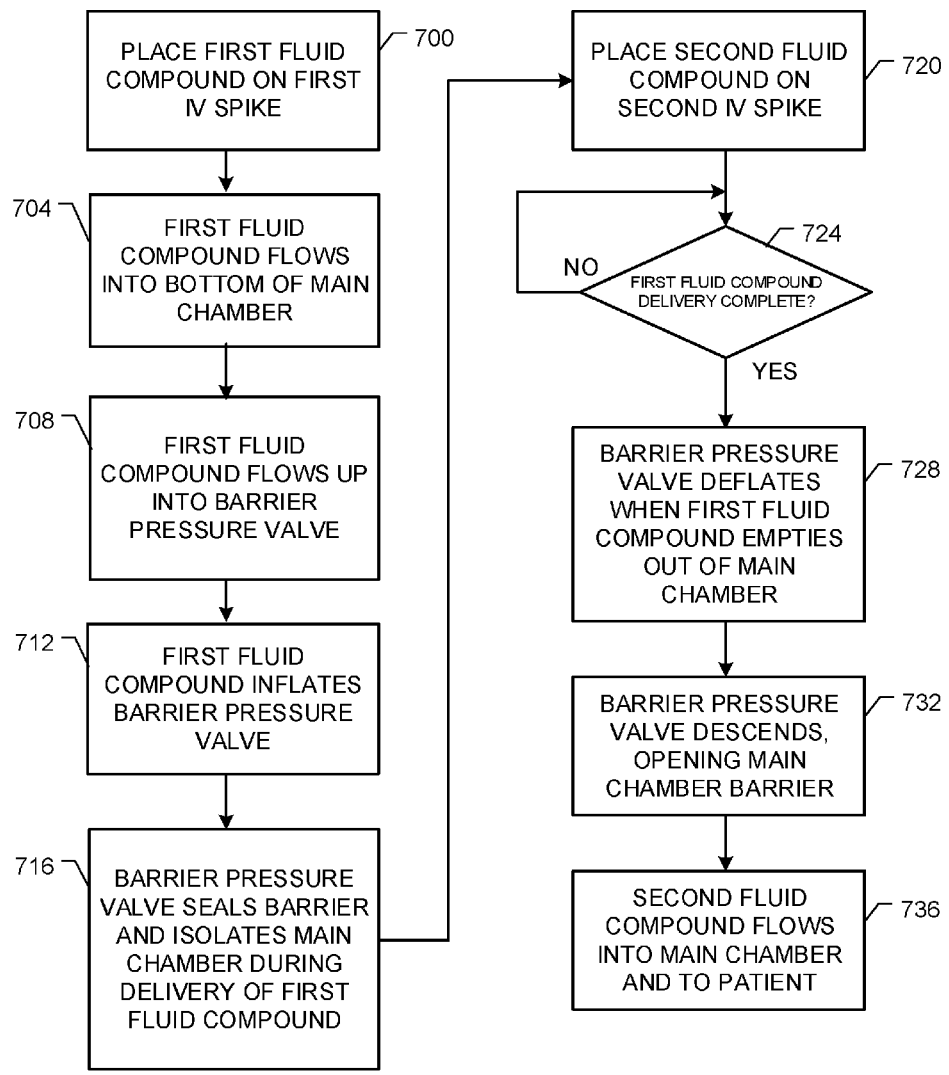
FIG. 7 is a flow layout for the operation of the IV isolation system using a barrier pressure valve for isolated delivery of two separate fluid compounds to a patient consistent with certain embodiments of the present invention.

Turning to FIG. 7, this figure presents an exemplary view of a process flow for the operation of the IV isolation system using a barrier pressure valve for isolated delivery of two separate fluid compounds to a patient consistent with certain embodiments of the present invention. The initial step in the process in 700 is when a medical staff member places an IV bag containing a first fluid compound on a first IV spike. In this system, the first IV spike is connected to the main chamber of the device through a flexible tube that is attached at one end to the first IV spike and the other end of the flexible tube is attached to the main chamber of the device through a side entry point. After attachment, at 704 the first fluid compound flows from the first IV bag, through the IV spike and associated flexible tube and into the bottom portion of the main chamber of the device. At 708, the first fluid compound impacts the side point directly opposite to the side entry point and spreads vertically upward and downward from the impact point to flow into the barrier pressure valve and the bottom part of the main chamber. At 712, as more of the first fluid compound flows into the main chamber, the barrier pressure valve move upward vertically under the pressure of the first fluid compound until the barrier pressure valve is stopped by the barrier portion of the main chamber. As the first fluid compound continues to flow, the first fluid compound inflates a flexible portion of the barrier pressure valve that is now in a position vertically above the barrier portion of the main chamber. At 716, the first fluid compound continues to inflate the flexible portion of the barrier pressure valve until the flexible portion comes into contact with the interior surface walls of the upper portion of the main chamber, sealing the opening to the bottom portion of the main chamber and isolating the top portion from the bottom portion of the main chamber during the delivery of the first fluid compound.

At 720, after the top portion of the main chamber is isolated from the bottom portion of the main chamber by the barrier pressure valve, a medical staff person may then place a second IV bag containing a second fluid compound on a second IV spike. The second fluid compound will flow into the top portion of the main chamber through the flexible tube that connects the second IV spike with the top entry point of the main chamber. The second fluid compound will now fill the top portion of the main chamber, but remain contained and isolated from the first fluid compound and the bottom portion of the main chamber. At 724, if the first fluid compound has not completely emptied out of the first IV bag, the barrier pressure valve will remain inflated and continue to isolate the top portion of the main chamber from the bottom portion of the main chamber. If the first fluid compound has completely emptied out of the first IV bag, the delivery of the first fluid compound to the patient is completed.

At 728, the absence of the first fluid compound now permits the flexible portion of the barrier pressure valve to deflate. At 732, the pressure of the second fluid compound against the deflated barrier pressure valve causes the barrier pressure valve to descend into the bottom portion of the main chamber, unsealing the top portion and permitting the second fluid compound to flow from the top part of the main chamber, past the barrier pressure valve. At 736, the second fluid compound is now able to flow into the bottom portion of the main chamber and downward through the IV spike connected to the flexible tube that permits the flow of the second fluid compound to the patient. In this manner, two fluid compounds may be connected to the device quickly, while the device isolates the delivery of the two fluid compounds without further intervention of a medical staff person.

While certain illustrative embodiments have been described, it is evident that many alternatives, modifications, permutations and variations will become apparent to those skilled in the art in light of the foregoing description.

What is claimed is:

1. A device for isolated delivery of fluid compounds, comprising:
    a main chamber having a top portion, barrier portion, and bottom portion;
    the main chamber having at least two entry points and one exit point for fluid flow;
    a barrier pressure valve installed wholly within the main chamber and positioned to permit the barrier pressure valve to move vertically through an opening in the center of the barrier portion of the main chamber;
    the barrier pressure valve having a flexible portion and a rigid portion;
    the barrier pressure valve positioned such that when the flexible portion is filled with a fluid, the flexible portion is above the barrier portion of the main chamber and contained within the top portion of the main chamber; and
    the flexible portion of the barrier pressure valve is sufficiently flexible to inflate under the pressure of a fluid introduced to the main chamber and cause the barrier pressure valve to isolate the top portion of the main chamber from the bottom portion of the main chamber such that no fluid may flow from the top portion of the main chamber to the bottom portion of the main chamber.

2. A device as in claim 1, wherein the top portion, barrier portion, and bottom portion of the main chamber are arranged vertically, with the top portion at the top, the bottom portion at the bottom and the top portion separated from the bottom portion by the barrier portion when the main chamber is held upright, and the entire device is composed of materials that may be sterilized such that the device is entirely sterile prior to use.

3. A device as in claim 2, wherein the barrier portion of the main chamber comprises an exterior cross section having the same cross section or diameter as the exterior cross section or diameter as the top and bottom portions of the main chamber, and the barrier portion has an internal cross section or diameter that is smaller than the interior cross section or diameter of the top and bottom portions of the main chamber.

4. A device as in claim 3, wherein the barrier portion of the main chamber has an opening in the center of the barrier portion.

5. A device as in claim 1, wherein a barrier pressure valve is positioned entirely within the main chamber.

6. A device as in claim 5, wherein the barrier pressure valve is positioned to move vertically through an opening in the center of the barrier portion of the main chamber.

7. A device as in claim 1, wherein the main chamber has a first entry point for fluid flow positioned in the side wall of the bottom portion of the main chamber, a second entry point for fluid flow positioned at the top edge of the top portion of the main chamber, and an exit point for fluid flow positioned at the bottom edge of the bottom portion of the main chamber.

8. A device as in claim 1, wherein the bottom portion of the main chamber has a flexible plastic membrane positioned vertically between the first entry point and the bottom edge of the bottom portion of the main chamber.

9. A device as in claim 6, wherein the barrier pressure valve has a flexible portion and a rigid portion, where the flexible portion is sufficiently flexible to inflate under the pressure of incoming fluid and come into contact with the interior surface of the top portion of the main chamber to form a seal between the flexible portion of the barrier pressure valve and the top portion of the main chamber that prevents the flow of fluid past the barrier pressure valve flexible portion.

10. A system for isolated delivery of fluid compounds, comprising:
a main chamber having a top portion, barrier portion, and bottom portion;
the main chamber having at least two entry points and one exit point for fluid flow;
a barrier pressure valve installed wholly within the main chamber and positioned to permit the barrier pressure valve to move vertically through an opening in the center of the barrier portion of the main chamber;
the barrier pressure valve having a flexible portion and a rigid portion;
the barrier pressure valve positioned such that when the flexible portion is filled with a fluid, the flexible portion is above the barrier portion of the main chamber and contained within the top portion of the main chamber and the rigid portion is in contact with the barrier portion of the main chamber; and
the flexible portion of the barrier pressure valve is sufficiently flexible to inflate under the pressure of a fluid introduced to the main chamber and cause the barrier pressure valve to isolate the top portion of the main chamber from the bottom portion of the main chamber such that no fluid may flow from the top portion of the main chamber to the bottom portion of the main chamber.

11. A system as in claim 10, wherein the top portion, barrier portion, and bottom portion of the main chamber are arranged vertically, with the top portion at the top, the bottom portion at the bottom and the top portion separated from the bottom portion by the barrier portion when the main chamber is held upright, and the entire device is composed of materials that may be sterilized such that the device is entirely sterile prior to use.

12. A system as in claim 11, wherein the barrier portion of the main chamber comprises an exterior cross section having the same cross section or diameter as the exterior cross section or diameter as the top and bottom portions of the main chamber, and the barrier portion has an internal cross section or diameter that is smaller than the interior cross section or diameter of the top and bottom portions of the main chamber.

13. A system as in claim 12, wherein the barrier portion of the main chamber has an opening in the center of the barrier portion.

14. A system as in claim 10, wherein a barrier pressure valve is positioned entirely within the main chamber.

15. A system as in claim 14, wherein the barrier pressure valve is positioned to move vertically through an opening in the center of the barrier portion of the main chamber.

16. A system as in claim 10, wherein the main chamber has a first entry point for fluid flow positioned in the side wall of the bottom portion of the main chamber, a second entry point for fluid flow positioned at the top edge of the top portion of the main chamber, and an exit point for fluid flow positioned at the bottom edge of the bottom portion of the main chamber.

17. A system as in claim 10, wherein the bottom portion of the main chamber has a flexible plastic membrane positioned vertically between the first entry point and the bottom edge of the bottom portion of the main chamber.

18. A system as in claim 17, wherein the barrier pressure valve has a flexible portion and a rigid portion, where the flexible portion is sufficiently flexible to inflate under the pressure of incoming fluid and come into contact with the interior surface of the top portion of the main chamber to form a seal between the flexible portion of the barrier pressure valve and the top portion of the main chamber that prevents the flow of fluid past the barrier pressure valve flexible portion.

* * * * *